United States Patent [19]

Baggiolini et al.

[11] 4,021,423
[45] May 3, 1977

[54] SYNTHESES OF 24R,25- AND 24S,25-DIHYDROXYCHOLECALCIFEROL

[75] Inventors: Enrico Baggiolini, Nutley; John Joseph Partridge, Jr.; Milan Radoje Uskokovic', both of Upper Montclair, all of N.J.

[73] Assignee: Hoffmann-La Roche Inc., Nutley, N.J.

[22] Filed: Mar. 8, 1976

[21] Appl. No.: 664,799

[52] U.S. Cl. .................... 260/239.55 D; 260/397.2
[51] Int. Cl. ........................................... C07j 71/00
[58] Field of Search ................ 260/397.2, 239.55 D

[56] References Cited

UNITED STATES PATENTS 3,901,928   8/1975   Hesse et al. .................... 260/397.2

OTHER PUBLICATIONS

Seki et al., "Tetrahedron Letters", (1975), No. 15.
Lam et al., "Biochemistry", (1973), vol. 12, pp. 4851–4854.

Primary Examiner—Elbert L. Roberts
Attorney, Agent, or Firm—Samuel L. Welt; George M. Gould; Raymond R. Wittekind

[57] ABSTRACT

Syntheses of 24R,25- and 24S,25-dihydroxycholecalciferol, the biologically important metabolite and derivative, respectively, of vitamin $D_3$, are described.

17 Claims, No Drawings

SYNTHESES OF 24R,25- AND 24S,25-DIHYDROXYCHOLECALCIFEROL

BACKGROUND OF THE INVENTION

The isolation and characterization of 24,25-dihydroxycholecalciferol (24,25-dihydroxyvitamin $D_3$) (M. F. Holick et al., Biochemistry, 11, 4251 [1972]), and the subsequent finding that this second most abundant metabolite of vitamin $D_3$ (J. L. Omdahl and H. F. DeLuca, Physiological Reviews, 53, 327 [1973]) preferably stimulates intestinal calcium transport without, at comparable dose levels, mobilizing bone calcium, prompted extensive investigation of the physiological role played by this metabolite (see, for example, H. K. Schnoes and H. F. DeLuca, Vitamins and Hormones, 32, 395 [1974]). These investigations have been hampered by the minute amounts of the metabolite available from natural sources, the lack of information concerning the stereochemistry of the metabolic hydroxyl group at C-24 and the effect of the configuration of this group on the biological activity exhibited by 24,25-dihydroxycholecalciferol.

In 1973, M. Seki et al., Chem. Pharm. Bull. (Japan), 21, 2783 (1973) described the conversion of desmosterol acetate to 24 $\xi$,25-dihydroxycholesterol, a precursor of 24,25-dihydroxycholecalciferol. Shortly thereafter, H.-Y. Lam et al., Biochemistry, 12, 4851 (1973) and J. Redel et al., Compt. rend. Acad. Sci. (Paris), 278, 529 (1974) disclosed syntheses of 24 $\xi$,25-dihydroxycholecalciferol starting from 3 $\beta$-acetoxy-27-nor-5-cholesten-25-one and desmosterol acetate, respectively. These syntheses are non-stereosphecific yielding mixtures of stereoisomers at C-24. M. Seki et al., Tetrahedron Letters, 15 (1975) recently described the separation of 24 $\xi$,25-dihydroxycholesterol into the 24R- and 24S-isomers and the conversion of the 24R- and 24S- isomers into 24R,25- and 24S,25-dihydroxycholecalciferol, respectively. This synthesis suffers from the inherent disadvantages associated with the separation step. Thus, stereospecific syntheses of 24R,25- and 24S,25-dihydroxycholecalciferol utilizing 24,25-dihydroxycholesterol derivatives of known stereochemistry at C-24 overcoming the deficiencies of the prior art processes and making this important metabolite of vitamin $D_3$ readily available for biological, clinical and therapeutic use would represent an important contribution to the advancement of the state of the art in the vitamin D field.

DETAILED DESCRIPTION OF THE INVENTION

The present invention relates to a novel efficient process for the preparation of 24R,25- and 24S,25-dihydroxycholecalciferol starting from precursors readily available from natural sources. More particularly, the present invention relates to methods of syntheoizing 24R,25 - and 24S,25-dihydroxycholecalciferol comprising the steps of photolyzing 3,24R,25- and 3,24S,25-trihydroxy-5,7-cholestadiene 24,25-ketals and alkanoyl derivatives thereof to 24R,25- and 24S,25-dihydroxyprecholecalciferol ketals and alkanoyl derivatives thereof, isomerizing 24R,25- and 24S,25-dihydroxyprecholecalciferol ketals and alkanoyl derivatives thereof to 24R,25- and 24S,25-dihydroxycholecalciferol ketals and alkanoyl derivatives thereof, deketalizing and saponifying, if necessary, 24R25- and 24S,25-dihydroxycholecalciferol, ketals and alkanoyl derivatives thereof to 24R,25- and 24S,25-dihydroxycholecalciferol.

As used throughout the specification and the appended claims, the term "alkyl group" refers to a monovalent substituent consisting solely of carbon and hydrogen of from 1 to 20 carbon atoms which may be straight or branched-chain. Examples of alkyl groups are methyl, ethyl, n-propyl, i-propyl, tert.-butyl, hexyl, octyl and so forth. The term "alkylene group" refers to a divalent substituent consisting solely of carbon and hydrogen of from 1 to 20 carbon atoms which may be straignt or branched-chain and whose free valences are attached to two distinct groups. Examples of alkylene groups are methylene, ethylene, propylene and so forth. The term "alkoxy group" refers to a monovalent substituent which consists of an alkyl group linked through an ether oxygen having its free valence bond from the ether oxygen. Examples of alkoxy groups are methoxy, ethoxy, isopropoxy, tert.-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups are formyloxy, acetoxy, butyryloxy, hexanoyloxy and so forth. The term "substituted" as applied to "phenyl" refers to phenyl which is substituted with one or more of the following groups: alkyl, halogen (i.e., fluorine, chlorine, bromine or iodine), nitro, cyano, trifluoromethyl and so forth. The term "alkanol" refers to a compound derived by protonation of the oxygen atom of an alkoxy group. Examples of alkanols are methanol, ethanol, 2-propanol, 2-methyl-2-propanol and the like. The term "lower" as applied to any of the aforementioned groups, refers to those groups having from 1 to 8 carbon atoms.

In the formulas presented herein, the various substituents are illustrated as joinned to the steroid nucleus by one of these notations: a solid line (—) indicating a substituent which is in the $\beta$-orientation (i.e., above the plane of the molecule), a dotted line (⋯) indicating a substituent which is in the $\alpha$-orientation (i.e., below the plane of the molecule), or a wavy line (∿) indicating a substituent which may be in the $\alpha$- or $\beta$-orientation. The formulas have all been drawn to show the compounds in their absolute stereochemical configurations. Since the starting materials are derived from naturally occurring stigmasterol, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively.

The Greek letter xi ($\xi$) in the name of a vitamin $D_3$ intermediate or metabolite indicates that the stereochemistry of the substituent to which it refers is undefined or that the product consists of a mixture of compounds epimeric at the designated position.

The nomenclaturé adopted to define absolute configuration of substituents bound to carbon atom 24 of the steroid nucleus is described in the Journal of Organic Chemistry, 34, 2849 (1970) under the title "IUPAC Tentative Rules for the Nomenclature of Organic Chemistry. Section E. Fundamental Stereochemistry".

In the first step of the process of the present invention for the preparation of 24R,25- and 24S,25-dihydroxycholecalciferol of the formula

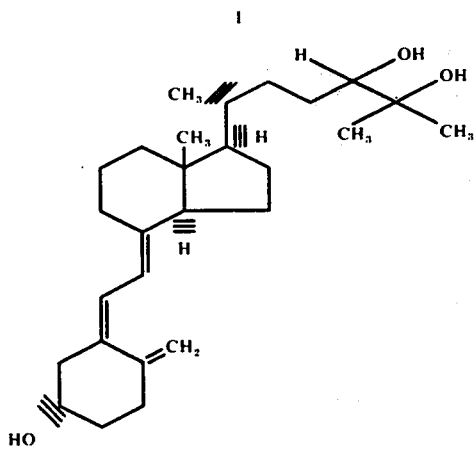

wherein the absolute configuration at C-24 is R or S 3,24R,25- and 3,24S,25-trihydroxy-5,7-cholestadiene 24,25-ketal and 3-alkanoyl derivatives thereof of the formula

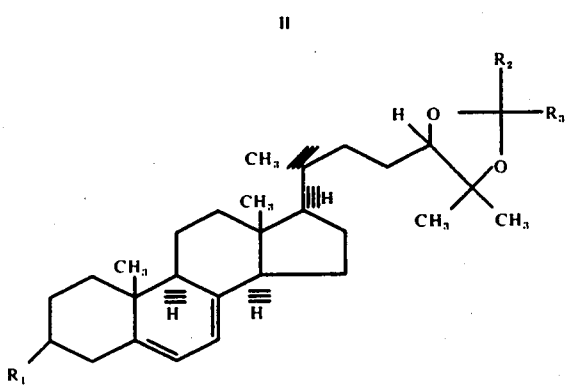

wherein $R_1$ is hydroxy or lower alkanoyloxy, $R_2$ and $R_3$ each independently are lower alkyl, $R_2$ and $R_3$ taken together are lower alkylene, and the absolute configuration at C-24 is R or S the preparation of which is described in U.S. Patent Application Ser. No. 664,848 filed of even date herewith, dissolved in a suitable organic solvent system is irradiated under an inert atmosphere by means of a mercury lamp equipped with a glass cooling finger at a temperature of about −40° to about +25° C., −5° C. being the preferred irradiation temperature, for the period of time necessary to effect about 50% conversion of the starting material.

Suitable inert atmospheres include nitrogen, helium, argon and the like.

Suitable sources of irradiation energy include high and low pressure mercury, xenon-mercury and thallium-mercury lamps. High pressure mercury lamps are preferred. A 450W Hanovia high pressure mercury lamp is the most preferred source of irradiation energy.

The glass cooling finger may be fabricated from Vycor or Corex glass or quartz.

Suitable inert organic solvent systems for the irradiation include mixtures of saturated aliphatic hydrocarbons, such as pentane, hexane, isooctane and the like, and ethereal solvents, such as monoglyme, diglyme, tetrahydrofuran, and the like.

Upon completion of the irradiation, the solvents are removed by evaporation and the residue is separated into pure 24R,25- or 24S,25-dihydroxyprecholecalciferol 24,25-ketals an alkanoyl derivatives thereof of the formula

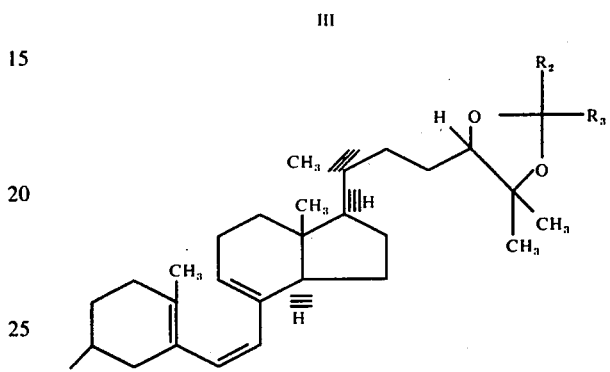

wherein $R_1$, $R_2$ and $R_3$ are as above and the absolute configuration at C-24 is R or S and pure unchanged 3,24R,25- or 3,24S,25-trihydroxy-5,7-cholestadiene 24,25-ketals and alkanoyl derivatives thereof of fformula II on a high pressure liquid chromatograph employing a solid absorbent column and an inert organic eluent. Suitable inert organic eluents for the separation step include mixtures of hydrocarbons, such as n-hexane, isooctane, benzene, toluene and the like and esters such as ethyl acetate, ethyl benzoate and the like. Suitable solid absorbents include Porasil, Corasil, Biosil, Zorbax, Zorbax-Sil, Sil-X and the like. A Waters Associates Chromatograph Model 202 using an 8-foot by ⅜ inch Porasil A column and a mixture of n-hexane/ethyl acetate as the eluent is the preferred high pressure liquid chromatographic system.

Unchanged 3,24R,25- or 3,24S,25-trihydroxy-5,7-cholestadiene 24,25-ketals and alkanoyl derivatives thereof are recycled through the irradiation process to obtain additional quantities of pure 24R,25- or 24S,25-dihydroxyprecholecalciferol 24,25-ketals and alkanoyl derivatives thereof, thereby rendering this crucial step of the process and the overall process highly efficient in comparison with related processes previously disclosed, for example, by D. H. R. Barton et al., J.C.S. Chem. Comm., 203 (1974) and by H. DeLuca et al., Tetrahedron Letters, 4147 (1972).

In the second step of the present process, 24R,25- and 24S,25-dihydroxyprecholecalciferol 24,25-ketals and alkanoyl derivatives thereof are isomerized to 24R,25- and 24S,25-dihydroxycholecalciferol 24,25-ketals and alkanoyl derivatives thereof the formula

IV

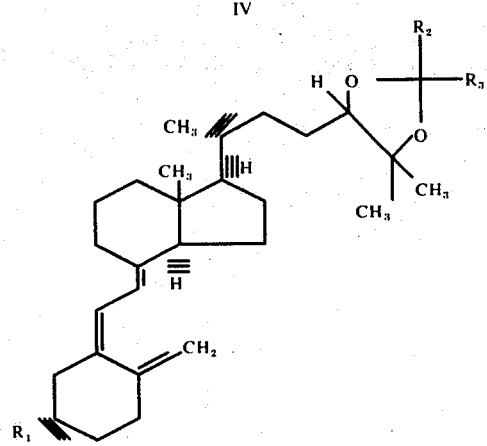

wherein $R_1$, $R_2$ and $R_3$ are as above and the absolute configuration at C-24 is R or S by heating the previtamin in an inert organic solvent, such as dioxane, tetrahydrofuran, monoglyme, diglyme and the like, under an inert atmosphere, such as argon, nitrogen, helium and the like, by methods well known in the art. See, for example, D. H. R. Barton et al., J.Am. Chem. Soc., 98, 2748 (1973).

In the final steps of the synthetic sequence, 24R,25- and 24S,25-dihydroxycholecalciferol 24,25-ketals and alkanoyl derivatives thereof are diketalized to 24R,25- and 24S,25-dihydroxycholecalciferol and alkanoyl derivatives thereof of the formula

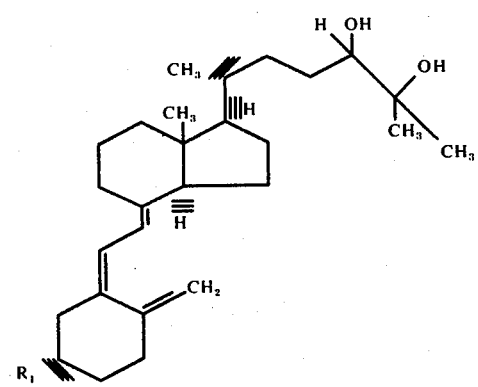

V wherein $R_1$ is as above and the absolute configuration at C-24 is R or S and, if necessary, saponified to 24R,25-and 24S,25-dihydroxycholecalciferol.

The deketalization is conducted by treating a compound of formula IV with an excess of an alkanol containing an aciid. Suitable acids include mineral acids, such as hydrogen chloride, hydrogen bromide, sulfuric acid, boron trifluoride and the like, organic acids such as para-toluenesulfonic acid, trifluoroacetic acid and the like, and cationic exchange resins in the hydrogen form such as Bio-Rad Ag 50W-X4, Bio-Rad AG 50W, Dowex 50W, Duolite C20, Amberlite IR, Zeocarb, Permutit Q, Nalcite and the like. Cationic exchange resins in the hydrogen form are preferred. Bio-Rad AG 50W-X4 is most preferred.

Suitable alkanols include methanol, ethanol, 2-propanol, 2-butanol, 2-pentanol and the like. Also include as suitable alkanols are aliphatic diols such as ethylene glycol, propylene glycol and the like. Alkanols are preferred, methanol being most preferred.

While the deketalization temperature is not critical, it is desirable to perform the reaction at a reduced temperature of between −20° C. and +20° C. to avoid the formation of side products. A deketalization temperature of about −5° C. is most preferred.

The saponification of compounds of formula V wherein $R_1$ is lower alkanoyloxy is performed by methods well known in the art. For example, the saponification can be accomplished by dissolving the alkanoyl derivatives of formula V in an alcoholic solution of an alkali metal hydroxide and allowing the solution to stand at a reduced temperature of about −20° C. to about +20° C., a reduced temperature of about 0° C. being preferred. It is also preferable to perform the saponification under an inert atmosphere of nitrogen, helium and the like. Suitable alcoholic solvents include methanol, ethanol, 2-propanol and the like. Suitable alkali metal hydroxides include sodium and potassium hydroxide. Methanol and potassium hydroxide are preferred.

The intermediates of the present invention as delineated herein are useful for the preparation of 24R,25- and 24S,25-dihydroxycholecalciferol.

The following examples are illustrative only of the invention and are not to be construed as limiting the invention in any manner.

EXAMPLE 1

24R,25-Dihydroxyprecholecalciferol 3-acetate 24,25-acetonide

A solution of 0.498 g. (0.001 mol) of 3S,24R,25-trihydroxy-5,7-cholestadiene 3-acetate 24,25-acetonide in 40 ml. of n-hexane and 40 m. of tetrahydrofuran was irradiated for 10 minutes at −5° C. and under argon using a 450W Hanovia high pressure mercury lamp, cooled with a Vycor-glass cooling finger. The solvents were then removed at 25° C. in vacuo and the residue purified with a Waters Associates liquid chromatograph Model 202 using a 8′ × ⅜″ Porasil A column and a 9:1 mixture of n-hexane/ethyl acetate as eluent to give 0.265 g. of 24R,25-dihydroxyprecholecalciferol 3-acetate 24,25acetonide as a thick oil.

EXAMPLE 2

24R,25-Dihydroxyprecholecalciferol 24,25-acetonide

A solution of 0.509 g. (0.00111 mol) of 3S,24R,25-trihydroxy-5,7-cholestadiene 24,25-acetonide in 40 ml. of n-hexane and 40 ml. of tetrahydrofuran was irradiated for 10 minutes at −5° C. and under argon using a 450W Hanovia high pressure mercury lamp, cooled with a Vycor-glass cooling finger. The solvents were then removed at 25° C. in vacuo and the residue purified with a Waters Associates liquid chromatograph Model 202 using a 8′ × ⅜″ Porasil A column and a 4:1 mixture of n-hexane/ethyl acetate as eluent to give 0.258 g. (50%) of 24R,25-dihydroxyprecholecalciferol 24,25-acetonide as a thick oil.

EXAMPLE 3

24S,25-Dihydroxyprecholecalciferol 3-acetate 24,25-acetonide

A solution of 0.518 g. (0.00104 mol) of 3S,24S,25-trihydroxy-5,7-cholestadiene 3-acetate 24,25-acetonide in 40 ml. of n-hexane and 40 ml. of tetrahydrofuran was irradiated for 10 minutes at −5° C. and under argon, using a 450W Hanovia high pressure mercury lamp, cooled with a Vycor-glass cooling finger. The solvents were then removed in vacuo at 25° C. and the residue purified with Waters Associates liquid chromatograph Model 202 using a 8′ × ⅜″ Porasil A column and a 9:1 mixture of n-hexane/ethyl acetate as eluent, to gives 0.220 g. of 24S,25-dihydroxyprecholecalciferol 3-acetate 24,25-acetonide as a thick oil.

EXAMPLE 4

24S,25-Dihydroxyprecholecalciferol 24,25-acetonide

A solution of 0.477 g. (0.00104 mol) of 3S,24S,25-trihydroxy-5,7-cholestadiene 24,25-acetonide in 40 ml. of n-hexane and 40 ml. of tetrahydrofuran was irradiated for 10 minutes at −5° C. and under argon, using a 450W Hanovia high pressure mercury lamp, cooled with a Vycor-glass cooling finger. The solvents were then removed in vacuo at 25° C. and the residue purified with a Waters Associates liquid chromatograph Model 202 using a 8′ × ⅜″ Porasil A column and a 4:1 mixture of n-hexane/ethyl acetate as eluent to give 0.201 g. (42%) of 24S,25-dihydroxyprecholecalciferol 24,25-acetonide as a thick oil.

EXAMPLE 5

24R,25-Dihydroxycholecalciferol 3-acetate 24,25-acetonide

A solution of 0.250 g. (0.000502 mol) of 24R,25-dihydroxyprecholecalciferol 3-acetate 24,25-acetonide in 20 ml. of dioxane was refluxed under argon for one hour. The solvent was then removed in vacuo an the residue purified with a Waters Associates liquid chromatograph Model 202 using a 8′ × ⅜″ Porasil A column and a 9:1 mixture of n-hexane/ethyl acetate as eluent to give 0.200 g. of 24R,25-dihydroxycholecaliciferol 3-acetate 24,25-acetonide a thick oil.

EXAMPLE 6

24R,25-Dihydroxycholecalciferol 24,25-acetonide

A solution of 0.258 g. (0.000565 mol) of 24R,25-dihydroxyprecholecalciferol 24,25-acetonide in 20 ml. of dioxane was refluxed under argon for 1 hour. The solvent was then removed in vacuo and the residue purified with a Waters Associates liquid chromatograph Model 202 using a 8′ × ⅜″ Porasil A column and a 4:1 mixture of n-hexane/ethyl acetate as eluent to give 0.200 g. (77%) of 24R,25-dihydroxycholecalciferol 24,25-acetonide as a thick oil.

EXAMPLE 7

24S,25-Dihydroxycholecalciferol 3-acetate 24,25-acetonide

A solution of 0.200 g. (0.000401 mol) of 24S,25-dihydroxyprecholecalciferol 3-acetate 24,25-acetonide in 20 ml. of dioxane was refluxed under argon for one hour. The solvent was then removed in vacuo and the residue purified with a Waters Associates liquid chromatograph Model 202 using a 8′ × ⅜″ Porasil A column and a 9:1 mixture of n-hexane/ethyl acetate as eluent to give 0.170 g. of 24S,25-dihydroxycholecalciferol 3-acetate 24,25-acetonide as a thick oil.

EXAMPLE 8

24S,25-Dihydroxycholecalciferol 24,25-acetonide

A solution of 0.340 g. (0.000745 mol) of 24S,25-dihydroxyprecholecalciferol 24,25-acetonide in 20 ml. of dioxane was refluxed under argon for 1 hour. The solvent was then removed in vacuo and the residue purified with a Waters Associates liquid chromatograph Model 202 using a 8′ × ⅜″ Porasil A column and a 4:1 mixture of n-hexane/ethyl acetate as eluent to give 0.240 g. (70%) of 24S,25-dihydroxycholecalciferol 24,25-acetonide as a thick oil.

EXAMPLE 9

24R,25-Dihydroxycholecalciferol 3-acetate

A solution of 0.200 g. (0.000402 mol) of 24R,25-dihydroxycholecalciferol 3-acetate 24,25-acetonide in 5 ml. of methanol to which 0.500 g. of the hydrogen form of a cation exchange resin (Bio-Rad AG 50W-X4) was added and stirred under argon for 40 hours at −5° C. The reaction mixture was then filtered, the exchange resin washed with 3 × 10 ml. of methanol and the combined methanol phases evaporated in vacuo at 25° C. to give 0.173 g. of crude 24R,25-dihydroxycholecalciferol 3-acetate as a thick oil.

EXAMPLE 10

24R,25-Dihydroxycholecalciferol

A solution of 0.200 g. (0.000438 mol) of 24R,25-dihydroxycholecalciferol 24,25-acetonide in 5ml. of methanol to which 500 mg. of the hydrogen form of a cation exchange resin (Bio-Rad AG 50W-X4) was added, was stirred under argon for 40 hours at −5° C. The reaction mixture was then filtered, the exchange resin washed with 3 × 10 ml. of methanol and the combined methanol phases evaporated in vacuo at 25° C. The residue was purified by liquid chromatography, using a Waters Associates Model 202 liquid chromatograph and a 1:1 mixture of n-hexane/ethyl acetate as eluent to give 0.127 g. (70%) of 24R,25-dihydroxycholecalciferol. Crystallization from methyl formate gave 0.094 g. (40%) of the above product as white crystals, m.p. 136°–137° C.; $[\alpha]_D^{25}$ +113.0° (c 0.33, EtOH).

EXAMPLE 11

24S,25-Dihydroxycholecalciferol 3-acetate

A solution of 0.200 g. (0.00042 mol) of 24S,25-dihydroxycholecalciferol 3-acetate 24,25-acetonide in 5 ml. of methanol to which 0.500 g. of the hydrogen form of a cation exchange resin (Bio-Rad AG 50W-X4) was added and stirred under argon for 40 hours at −5° C. The reaction mixture was then filtered, the exchange resin washed with 3 × 10 ml. of methanol and the combined methanol phases evaporated in vacuo at 25° C. to give 0.168 g. of crude 24S,25-dihydroxycholecalciferol 3-acetate as a thick oil.

EXAMPLE 12

24S,25-Dihydroxycholecalciferol

A solution of 0.170 g. (0.000372 mol) of 24S,25-dihydroxycholecalciferol 24,25-acetonide in 5 ml. of methanol to which 500 mg. of the hydrogen form of a cation exchange resin (Bio-Rad AG 50W-X4) was added, was stirred under argon for 40 hours at −5° C. The reaction mixture was then filtered, the exchange resin washed with 3 × 10 ml. of methanol and the combined methanol phases evaporated in vacuo at 25° C. The residue was purified by liquid chromatography, using a Waters Associates Model 202 liquid chromatograph and a 1:1 mixture of n-hexane/ethyl acetate as eluent to give 0.086 g. (60%) of 24S,25-dihydroxycholecalciferol. Crystallization from methyl formate gave 0.045 g. (29%) of the above product as white crystals, m.p. 111°–112° C.; $[\alpha]_D^{25}$ +93.7° (c 0.3, EtOH).

EXAMPLE 13

24R,25-Dihydroxycholecalciferol

A solution of 0.173 g. (0.000377 mol) of crude 24R,25-dihydroxycholecalciferol 3-acetate (see Example 9) and 0.200 g. (0.00356 mol) of potassium hydroxide in 5 ml. of methanol were stirred at 0° C. under argon for 6 hours. The methanol was then evaporated in vacuo and the residue mixed with 30 ml. of water and extracted with 3 × 50 ml. of methylene chloride. The combined organic phases were washed with 3 × 30 ml. of saturated brine, dried over sodium sulfate, filtered and evaporated in vacuo at 25° C. The residue was purified by liquid chromatography, using a Waters Associates Model 202 liquid chromatograph and a 1:1 mixture of n-hexane/ethyl acetate as eluent to give 0.132 g. (84%) of 24R,25-dihydroxycholecaliciferol. Crystallization from methyl formate gave 0.098 g. of the above product as white crystals, m.p. 136°–137° C.

EXAMPLE 14

24S,25-Dihydroxycholecalciferol

A solution of 0.168 g. (0.000366 mol) of crude 24,S,25-dihydroxycholecalciferol 3-acetate (See Example 11) and 0.200 g. (0.00356 mol) of potassium hydroxide in 5 ml. of methanol were stirred at 0° C. under argon for 6 hours. The methanol was then evaporated in vacuo and the residue mixed with 30 ml. of water and extracted with 3 × 50 ml. of methylene chloride. The combined organic phases were washed with 3 × 30 ml. of saturated brine, dried over sodium sulfate, filtered and evaporated in vacuo at 25° C. The residue was purified by liquid chromatography, using a Waters Associates Model 202 liquid chromatograph and a 1:1 mixture of n-hexane/ethyl acetate as eluent to give 0.126 g. (82%) of 24S,25-dihydroycholecalciferol. Crystallization from methyl formate gave 0.085 g. of the above product as white crystals, m.p. 111°–112° C.

EXAMPLE 15

24R,25-Dihydroxyprecholecalciferol 24,25-acetonide

A solution of 0.500 g. (0.0011 mol) of 3S,24R,25-trihydroxy-5,7-cholestadiene 24,25-acetonide in 100 ml. of tetrahydrofuran was irradiated for 10 minutes at −5° C. and under argon using a 450W Hanovia high pressure mercury lamp, cooled with a Vycor-glass cooling finger. The solvents were removed at 25° C. in vacuo and the residue purified with a Waters Associates liquid chromatograph Model 202 using a 8' × ⅜" Porasil A column and a 4:1 mixture of n-hexane/ethyl acetate as eluent to give 0.274 g. of 24R,25-dihydroxyprecholecalciferol 24,25-acetonide as a thick oil and 0.125 g. of unreacted starting material.

We claim:

1. A compound of the formula

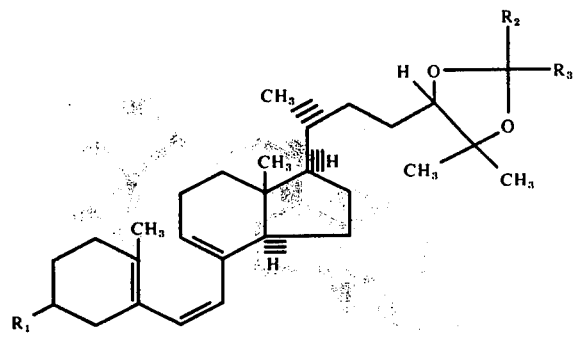

wherein $R_1$ is hydroxy or lower alkanoyloxy, $R_2$ and $R_3$ each independently are lower alkyl, $R_2$ and $R_3$ taken together are lower alkylene and the absolute configuration at C-24 is R or S.

2. The compound of claim 1 wherein $R_2$ and $R_3$ each independently are lower alkyl.

3. The compound of claim 2 which is 24R,25-dihydroxyprecholecalciferol 3-acetate 24,25-acetonide.

4. The compound of claim 2 which is 24R,25-dihycroxyprecholecalciferol 24,25-acetonide.

5. The compound of claim 2 which is 24S,25-dihydroxyprecholecalciferol 3-acetate 24,25-acetonide.

6. The compound of claim 2 which is 24S,25-dihydroxyprecholecalciferol 24,25-acetonide.

7. A compound of the formula

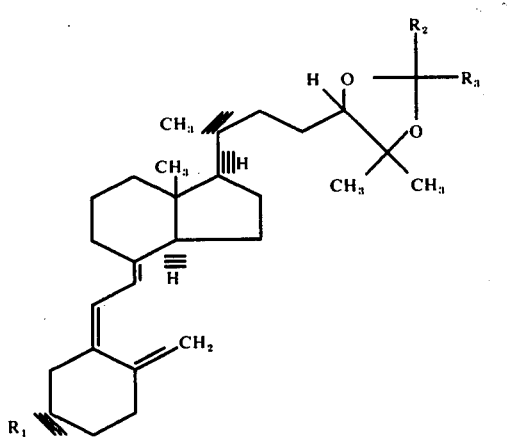

wherein $R_1$ is hydroxy or lower alkanoyloxy, $R_2$ and $R_3$ each independently are lower alkyl, $R_2$ and $R_3$ taken together are lower alkylene and the absolute configuration at C-24 is R or S.

8. The compound of claim 7 wherein $R_2$ and $R_3$ each independently are lower alkyl.

9. The compound of claim 8 which is 24R,25-dihydroxycholecalciferol 3-acetate 24,25-acetonide.

10. The compound of claim 8 which is 24R,25-dihydroxycholecalciferol 24,25-acetonide.

11. The compound of claim 8 which is 24S,25-dihydroxycholecalciferol 3-acetate 24,25-acetonide.

12. The compound of claim 8 which is 24S,25-dihydroxycholecalciferol 24,25-acetonide.

13. A process for the preparation of a compound of the formula

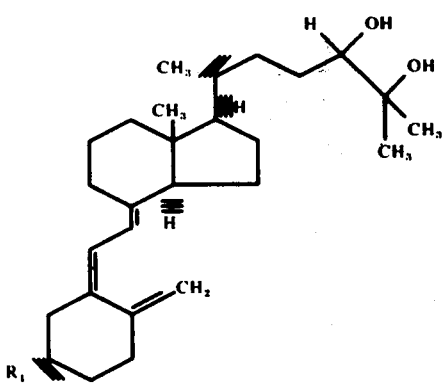

wherein $R_1$ is hydroxy or lower alkanoyloxy and the absolute configuration at C-24 is R or S which comprises contacting a compound of the formula

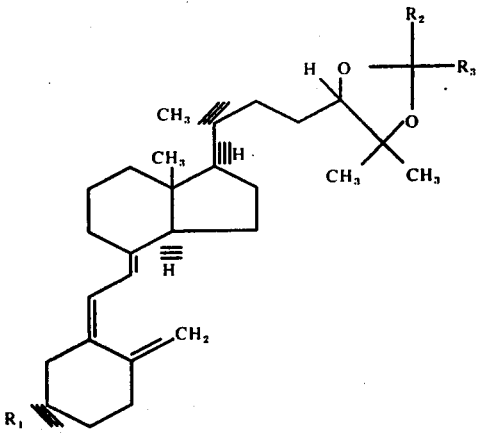

wherein $R_1$ is as above, $R_2$ and $R_3$ each independently are lower alkyl, $R_2$ and $R_3$ taken together are lower alkylene and the absolute configuration at C-24 is R or S with an acid and a hydroxylic solvent.

14. The process of claim 13 wherein the acid is an organic acid.

15. The process of claim 14 wherein the organic acid is para-toluenesulfonic acid.

16. The process of claim 13 wherein the hydroxylic solvent is an alkanol.

17. The process of claim 13 wherein the alkanol is methanol.

* * * * *